United States Patent [19]

Diebold et al.

[11] Patent Number: 5,543,299

[45] Date of Patent: Aug. 6, 1996

[54] EXTENDER CONTAINING POLYMER COMPOSITIONS AND USES THEREOF

[75] Inventors: Eric Diebold, Fishers; Myron Rapkin, Indianapolis; Abol Azhar, Fishers, all of Ind.; Arthur Usmani, Kuwait, Kuwait

[73] Assignee: Boehringer Mannheim Corporation, Indianapolis, Ind.

[21] Appl. No.: 368,810

[22] Filed: Jan. 5, 1995

Related U.S. Application Data

[63] Continuation of Ser. No. 52,485, Apr. 23, 1993, abandoned.

[51] Int. Cl.$^6$ ............... C12Q 1/28; C12Q 1/54; C12Q 1/00; C12Q 1/32
[52] U.S. Cl. ............... 435/28; 435/14; 435/4; 435/25; 435/19; 435/26; 435/20; 435/21; 436/501; 436/63; 436/810; 436/95; 436/169
[58] Field of Search ............... 435/28, 14, 4, 435/25, 19, 26, 20, 21; 436/501, 63, 810, 95, 169

[56] References Cited

U.S. PATENT DOCUMENTS

| | | | |
|---|---|---|---|
| 3,916,057 | 10/1975 | Hatch et al. | 428/236 |
| 3,968,089 | 7/1976 | Cuscurida et al. | 521/137 |
| 4,021,384 | 5/1977 | Brader, Jr. et al. | 521/137 |
| 4,657,739 | 4/1987 | Yasuda et al. | 422/56 |
| 4,689,309 | 8/1987 | Jones | 436/95 |
| 4,868,106 | 9/1989 | Ito et al. | 430/7 |
| 4,966,856 | 10/1990 | Ito et al. | 436/170 |
| 5,260,195 | 11/1993 | Azhar | 435/25 |

FOREIGN PATENT DOCUMENTS 825192  1/1982  Japan .

Primary Examiner—John Kight, III
Assistant Examiner—Louise N. Leary
Attorney, Agent, or Firm—Felfe & Lynch

[57] ABSTRACT

The invention relates to polymeric compositions useful in analyte determination. The compositions contain a polymer, a reagent system for analyte determination, and an extender. The last component alleviates tackiness in the composition, and thus reduces damage in preparation of test apparatus. Mica is the particularly preferred extender.

22 Claims, No Drawings

EXTENDER CONTAINING POLYMER COMPOSITIONS AND USES THEREOF

This application is a continuation of U.S. patent application Ser. No. 08/052,485, filed Apr. 23, 1993, now abandoned.

FIELD OF THE INVENTION

This invention relates to polymer containing compositions useful in the preparation of diagnostic and analytical devices. More particularly, it relates to compositions which alleviate a number of problems associated with the preparation of such devices.

BACKGROUND AND PRIOR ART

The fields of clinical and analytical chemistry utilize many devices and apparatuses for studying analytes in samples. An entire subfield, referred to hereafter as "dry chemistry techniques" involves the production of devices which can be used to carry out sample analyses. These devices facilitate prompt and accurate measurement of particular substances. They are easy to use, thereby permitting patient self testing, "over the counter" use, and so forth.

A particularly useful form of a dry chemistry device is the test strip. While there are a vast number of test strips available, they can be described generally. In brief, a test strip involves a matrix which can receive a test sample. The matrix usually contains one or more reagents impregnated or somehow incorporated therein, which combine with the substance of interest (the "analyte") in a reaction or series of reactions leading to generation of some detectable signal, e.g., a color. The matrix is usually supported by some non-reactive material, such as a thermoplastic or cellulose base.

The matrix of these test devices must be made of a material which does not deteriously effect the reaction leading to the previously mentioned detectable signal. Further, it must be sturdy and stable. These qualities are important, because test strips are usually stored for at least a short period of time before use, and deterioration of the matrix would interfere with the use of the strip in analyte determination. To this end, the materials used to make the matrices are preferably polymers. Examples of polymers which are used in preparing such matrices may be found in, e.g., PCT Application PCT/US91/09819, assigned to the assignee of the subject application, as well as in U.S. Pat. Nos. 4,966,856 to Ito et al., 4,689,309 to Jones, and 4,868,106, to Ito et al. All of the foregoing references are incorporated by reference. Also incorporated by reference are U.S. Pat. Nos. 4,786,595 to Arai et al., U.S. Pat. No. 4,576,793 to Koyama et al., U.S. Pat. No. 4,427,632 to Okaniwa et al., U.S. Pat. No. 4,258,001 to Pierce et al., U.S. Pat. No. 4,147,76, to Levy et al., and U.S. Pat. No. 4,060,678 to Stickler. Some of the polymers disclosed in these references are summarized infra, and show the diverse types of polymers useful in test strip manufacture.

In preparing matrices of the type described herein, the reagents necessary for the diagnostic reaction are incorporated, preferably via a liquid medium with the matrix polymer. The resulting solution, suspension, emulsion, e.g., is then poured or otherwise dispensed so as to form a thin film. The film is treated so as to remove the liquids present therein, and the resulting film is rolled and stored. In order to prepare test strips using the matrix, appropriate lengths of film are unrolled and converted to the desired size.

A serious problem in this procedure is that many polymer films, even when dry, exhibit a residual tackiness, stickiness, or blocking which is not surprising when one considers that many of the polymers are also used as adhesives, floor polishes, and the like. When rolled, the coatings or films adhere to each other, and when unrolled, there is tearing or blocking and other deterioration caused because of the tackiness. As a result, there is a need for polymer materials treated so as to eliminate or to reduce tackiness and consequently to eliminate the problems discussed supra. Any approach taken to solving this problem, however, must also consider whether the materials incorporated into the film, i.e., the reagents useful for analyte determination are damaged via the treatment.

In PCT application PCT/US91/09819, non-aqueous polymer systems are described. These systems are used to prepare reagent films useful in determining analytes. This reference is silent, however, with respect to water based polymer systems, such as aqueous polymer emulsions and solutions. Compositions of this category are the subject of the present invention.

It has now been found, surprisingly, that polymer films of the type described herein can be made in a manner which alleviates the tackiness problem without interfering with the reagents included in the film.

The invention is described in greater detail in the detailed description of preferred embodiments which follows.

EXAMPLE 1

A composition in the form of an aqueous emulsion was prepared, containing the following material:

| | |
|---|---|
| "UCAR 464"* Emulsion Polymer | 51.0 g |
| 15% sodium dodecylbenzene sulfonate | 10.0 g |
| glucose oxidase | 20 Ku |
| peroxidase | 41.4 Ku |
| 3,3',5,5' tetra-methyl benzidine ("TMB") | 0.74 g |
| polyvinyl pyrrolidone ("PVP") | 4.0 g |
| Igepal CO-530 (a nonionic surfactant) | 1.5 g |
| hexanol | 5.0 g |
| 1-methoxy 2-propanol (solvent for TMB) | 13.2 g |

*UCAR 464 is a tradename for a styrene acrylic latex produced by Union Carbide. It is an aqueous emulsion polymer, 50% solids and 50% water.

The composition was coated onto a polycarbonate film, lightly pigmented with $TiO_2$ (approximately 140 mµ). The resulting wet film had a thickness ranging from 50–150 µm. The films were dried at 50° C.±20° C. for 15 minutes. The films appeared to be dry and to the touch, were tack free. They were rolled for storage, as is standard for such materials. Upon unwinding, however, there was extensive damage to the coating surface due to the adhesive properties and tackiness of the coating.

In order to address the problem, ultrafine grade mica (C4000, 8 grams) was incorporated into the composition prior to drying. All other parameters were exactly the same. The resulting films were rolled, and, upon unwinding, showed no damage whatsoever.

Additional experiments were carried out using other extenders, including 325 white wet ground mica, C-1000 micro-mica, muscovite mica, 264 mica 325 mesh, ground mica, and polymica 325. The foregoing are materials which differ in particle size with respect to each other. All types of extender yielded a composition which, when dried, produced a tack free film.

In preparing the films, the amount of polymer relative to the amount of mica may vary. A successful film can be produced with a ratio as high as 10:0.1 (polymer/mica), or as low as about 5:1.

EXAMPLE 2

The composition described in Example 1 was changed by removing the mica and using, in its stead, 8 grams of clay, i.e., "Hydrite UF", available from Georgia Kaolin Company. The clay has a median particle size of about 0.2 μ, and a pH of anywhere from 4.2 to 5.2. It gives a residue maximum of 0.03% with 325-Mesh. The references to "residue maximum" and "325-Mesh" involve information well known in the art. To elaborate, the particles in a given sample may not be uniform, and have diameters over a range of values. Similarly, the art uses a number of screens, with openings of various size, to determine particle size of a test material. For example, a screen of "325-mesh" has openings that are about 44 microns in diameter. A substance that leaves 0.03% residue when used with a 325-Mesh screen consists almost entirely of particles smaller than 44 microns in diameter.

The resulting emulsion yielded a tack free film as did the mica containing composition. Further experiments combined both mica and clay in the same composition. The resulting films remained tack free.

EXAMPLE 3

Another film was prepared, using a polyvinyl acetate polymer, i.e., "UCAR-130". The formulation is as follows:

| | |
|---|---|
| UCAR-130 | 400.0 g |
| Tritox X-100 (15% solution) | 26.0 g |
| Igepal Co-530 | 6.0 g |
| 1.6 M MnSO$_4$ (in water) | 23.2 g |
| 1.3 M NiCl$_2$ (in water) | 23.2 g |
| Deionized water | 36.0 g |
| Phenazine ethanesulfate | .8012 g |
| Total: | 519.2 g |

This mixture produced a slurry. A portion of it (250.0 g) was then combined with a total of 18.5 g of C-4000 micromica, which is about 6.9% by weight. The slurry was filtered through a 100 μ filter bag, and then coated and dried in the same manner as were the films of Examples 1 and 2. The resulting material, when dried, formed a useful film, performing in the same way the films of Examples 1 and 2 did.

The foregoing demonstrates that the problem of tackiness in polymer based compositions, especially films, can be alleviated via the incorporation of a tack reducing extender to the polymeric material. This extender is added in an amount sufficient to alleviate tackiness in the resulting film, with the proviso that the amount so incorporated is not so high that it deleteriously effects the intended function of the film in which it is incorporated. These limits on the amount of incorporated extender will vary, but as indicated supra, the effect of the extender on the film can be easily determined via, e.g., rolling and unwinding a film containing the polymer and the extender to test for damage. Thus, routine experimentation will permit the artisan to test various concentrations of material.

The nature of the extender will vary, mica and clay being especially preferred, ultrafine grades being particularly preferred. When mica or clay is used, the amount may vary, with a weight percent of from 1–25 being preferred. A more preferred range is of from 1–10% by weight, and the optimum range being 1– 3% by weight. Ultrafine mica is preferred, but other forms of mica, such as muscovite mica may be used. In addition, clays, whether treated or untreated may be used, as may clear fibrous materials, chopped to a size permitting incorporation into a film. Among the types of fibers that may be used are Orlon®, Dacron®, and ramie fibers. These fibers also serve to reinforce and strengthen the film produced. The percentages referred to supra for mica can also be used for these additional extenders, it being understood that more than one extender may be used, the total amount of the combination remaining within the aforementioned guidelines for good results.

The extender, can be any of the extenders used in the art, and may be used with any polymer, those polymers which can be used to make films for analytical test apparatus being especially preferred. Copolymers may be used in connection with the extenders, those copolymers being especially preferred containing monomers of formulas:

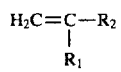

and

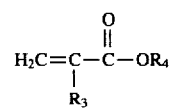

wherein each of $R_1$, $R_3$ and $R_4$ may be hydrogen, or C1–C6 alkyl, the alkyl group in each case being optionally substituted, and $R_2$ is a substituted or unsubstituted aromatic moiety. In an especially preferred embodiment, such as that described supra, the copolymer is a styrene/acrylic acid copolymer i.e., one where each of $R_1$, $R_3$ and R4 is hydrogen, and $R_2$ is a phenyl group.

The term reagent system as used herein refers to any material or combination of materials which, upon contact with an analyte of interest, provides a detectable signal indicative of the presence and/or amount of the analyte. For example, where the analyte of interest is glucose, the reagent system may contain glucose oxidase, horseradish peroxidase, and 3,3',5,5'-tetramethylbenzidine. These three components constitute a standard reagent system for analysis of glucose which is well known to the field. Other combinations will also be known to the artisan, including, e.g., systems using cholesterol specific enzymes, such as cholesterol oxidase, non enzymatic chemistries, and so forth. When these reagents are incorporated into analytical films in accordance with the invention, they may be in the form of solids, such as powders, encapsulated materials, emulsions, and so forth.

It has been noted, supra, that the compositions of the invention are preferably formed as films. Such films are useful in test strips and similar analytical devices. These devices generally include a film of the type indicated and an inert carrier. The film and carrier may be in direct contact, or there may be intervening materials in between.

It has been indicated, supra, that various polymers may be used in accordance with the invention. These include aqueous polymers and copolymers, and so forth. Emulsifiable polymers can also be used, as well as soluble polymers. Among the various polymers which can be used are the following:

(1) Poly(styrene-co-glycidyl methacrylate) [90/10], (2) poly(styrene-co-methyl acrylate-co-glycidyl methacrylate) [80/15/5], (3) poly(styrene-co-n-butyl methacrylate-co-glycidyl methacrylate) [75/15/10], (4) poly(styrene-co-vinylbenzyl chloride-co-glycidyl methacrylate) [80/10/10], (5) poly(styrene-co-divinylbenzene-co-glycidyl acrylate) [90/2/8], (6) poly(p-vinyltoluene-co-glycidyl methacrylate) [90/10], (7) poly(methacrylate-co-glycidyl methacrylate) [80/20], (8) poly(styrene-co-N,N-dimethylaminoethyl methacrylate) [95/5], (9) poly(styrene-co-aziridylethyl methacrylate) [95/5],

(10) poly(styrene-co-methyl acrylate co-acrolein) [90/5/5],

(11) poly(styrene-co-acrylamide) [95/5],

(12) poly(styrene-co-vinylthioly [95/5],

(13) poly(styrene-co-methylolated acrylamide) [95/5],

(14) poly(styrene-co-t-butyl acrylate-clycidyl methacrylate) [90/5/5],

(15) poly(styrene-co-vinyl isocyanate) [95/5],

(16) poly(methyl acrylate-co-styrene-co-N-methylolacrylamide) [50/35/15],

(17) poly(styrene-co-glycidyl methacrylate-co-N,N-dimethylaminoethyl methacrylate) [90/5/5],

(18) poly(styrene-co-methacrylic acid-co-acrylamide) [95/2/3],

(19) poly(co-N-methylolacrylamide-co-methoxyethyl acrylate) [90/5/5],

(20) poly(p-vinyltoluene-co-N-methylolacrylamide-co-acrylic acid) [90/8/2],

(21) poly(methyl methacrylate-co-glycidyl methacrylate-co-t-butyl acrylate) [80/10/10],

(22) poly(styrene-co-p-vinylbenzyl chloride-co-acrylic acid-co-ureidoethyl acrylate) [75/10/5/10],

(23) poly(styrene-co-methacrylein-co-α-hydroxyethyl methacrylate) 90/5/5],

(24) poly(styrene-co-acrolein-co-acetaceotxyethyl methacrylate) [85/5/10],

(25) poly(styrene-co-N,N-dimethylaminoethyl acrylate-co-vinylsulfonylethyl methacrylate) [90/5/5],

(26) poly(p-vinyltoluene-co-aminostyrene-co-vinylsulfonylethyl methacrylate) [85/10/5],

(27) poly(styrene-co-N,N-dimethylaminoethyl methacrylate) [90/10],

(28) poly(styrene-co-acrylic acid ) [97/3],

(29) poly)styrene-co-acrylamide) [97/3],

(30) poly(vinyltoluene-co-t-butyl acrylate) [95/5],

(31) poly(methyl acrylate-co-methacrylamide) [95/5],

(32) poly(styrene-co-N-methylolacrylamide) [95/5],

(33) poly(p-vinylbenzyl chloride-co-N-methylolacrylamide) [96/4],

(34) poly(styrene-co-itaconic acid) [98/2],

(35) poly(styrene-co-t-butyl acrylate) [92/8],

(36) poly(methyl acrylate-co-styrene-co-acrolein) [30/65/5],

(37) poly(methyl methacrylate-co-styrene-co-2-hydroxyethyl methacrylate) [25/70/30],

(38) poly(styrene-co-vinylsulfonylethyl acrylate) [80/20],

(39) poly(styrene-co-N,N-dimethylaminoethyl acrylate) [90/10],

(40) poly(styrene-co-methyl acrylate-co-acetacetoxyethyl acrylate [90/5/5], and

(41) poly(styrene-co-methacrylic acid) [95/5].

Additional polymers which may be used include acrylic copolymers, polyvinyl pyrrolidone co-styrene, polyvinylacetate, polyvinyl acetate-co-vinylethylene, polystyrene-co-butadiene, polyacrylonitrile, polyurethanes, biopolymers, gelatins, alginates, carrageenan, vinyl chlorides, vinyl propionates, ethylene vinyl acetates, melamines, melamine formaldehydes and urea formaldehydes.

With respect to the reagent system incorporated into the composition, this can be any material which leads to generation of a signal. Various enzymes, such as those recited in U.S. Pat. No. 4,966,856 may be incorporated into the composition. Examples of these include dehydrogenase, such as glycerol dehydrogenase, oxidases, including glucose oxidase; peroxidases, including horseradish peroxidases, esterases, such as cholesterol and choline esterase, phosphatases, such as alkaline phosphatases, galactosidases, amylases, and so forth. The enzymes may be combined in any suitable form, such as dry powder. In connection with these enzymes, specific substrates or indicators, including galactosides (e.g., p-nitrophenyl-β-D-galactoside), pyrogallols, gallic acid, 3,3', 5 5'-tetramethylbenzidine other Trinder type indicators, redox indicators, and so forth can be used.

As has been indicated, it is a basic requirement of the invention that an extender be used. "Extender", as the term is used herein, refers to any solid material which essentially acts as a diluent in a polymeric film. An example of a standard extender is "china clay", a common paint extender. Mica and clay are particularly preferred extenders, as discussed supra, but chopped fibers may also be used, as well as colloidal silica. As with all extenders, ultrafine grades are preferred.

Surfactants, such as sodium dodecyl sulfonate and sodium dodecyl sulfate may also be incorporated into the compositions. The surfactants may act to stabilize charged indicator molecules, to enhance color formation, and/or to enhance surface contact of the sample under analysis.

Throughout this disclosure, reference is made to "aqueous emulsion polymer" and/or "aqueous polymer emulsion", "Latex emulsion" and similar phraseology. These terms simply refer to systems where minute polymer particles are dispersed or suspended in a water matrix. When an emulsion is spread onto a support, the water evaporates and particles deform, as a result of capillary pressure. These move together, the polymer spheres frequently collapse, and the particles then stick together to yield a film. This film forming process can be enhanced by adding solvents, or by heating, so as to soften the polymers, thereby allowing sufficient deformation to form a film.

In preparing test apparatuses in accordance with the present invention, the matrix described supra is prepared in the form of a film, cut to desired size, and then incorporated into a test strip. This incorporation may involve as little as attaching the film matrix to an inert support via, e.g., hot melt adhesives, sewing, lamination, and so forth, or via integration into a more complex system as a component thereof. The preparation and production of such test strips is well known to the artisan, and need not be repeated here.

An alternate manner of making the test devices involves applying the matrix, in solution form, directly to the inert carrier or other support for the film. The composition can then be smoothed, raked, or otherwise treated to produce a smooth and uniform film upon drying. The resulting product can then be cut to size, and used "as is" or combined in a test device as appropriate and desired.

The manner in which such devices is used will be clear to the skilled artisan. Essentially, a sample to be analyzed is applied to the matrix, and the sample is taken up thereby. Any reactant in the sample which will react with the reagent system does so, leading to the generation of a detectable signal. Frequently this is formation of a color, but it need not be, changes in color, light reflection or absorption, etc., all being possible parameters for measuring. Electrochemical detection, including the use of electrodes and electrochemical biosensors are also embraced by the invention. Other uses of the compositions and test devices of the invention will be clear to the skilled artisan, and need not be repeated here.

It will be understood that the specification and examples are illustrative but not limitative of the present invention and that other embodiments within the spirit and scope of the invention will suggest themselves to those skilled in the art.

We claim:

1. The composition of matter comprising:
   (i) an aqueous polymer emulsion wherein said polymer is formed of at least one monomer selected from the group consisting of

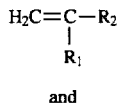

and

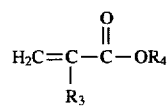

wherein $R_1$, $R_3$ and $R_4$, are the same or different, and are hydrogen or unsubstituted or substituted $C_1$–$C_6$ alkyl, and $R_2$ is a substituted or unsubstituted aromatic moiety;
   (ii) a reagent system for determination of an analyte; and
   (iii) an amount of an extender sufficient to reduce tackiness of said emulsion.

2. The composition of matter of claim 1, wherein said polymer is a copolymer.

3. The composition of matter of claim 2, wherein said copolymer is a copolymer of a first monomer of formula

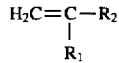

and a second monomer of formula

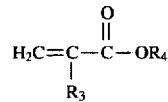

wherein $R_1$, $R_3$ and $R_4$, which may be the same or different, are hydrogen or unsubstituted or substituted C1–C6 alkyl, and $R_2$ is a substituted or unsubstituted aromatic moiety.

4. The composition of matter of claim 1, wherein said extender is mica.

5. The composition of matter of claim 1, wherein said extender is clay.

6. The composition of matter of claim 1, wherein said reagent system comprises an enzyme which reacts with said analyte to form a first reaction product and an indicator molecule which reacts with said reaction product or a second reaction product formed by reaction of said first reaction product and a reaction in said reactant system.

7. The composition of matter of claim 6, wherein said indicator is a dye.

8. The composition of matter of claim 6, wherein said enzyme is glucose oxidase.

9. The composition of matter of claim 8, wherein said reagent system further comprises peroxidase.

10. The composition of matter of claim 7, wherein said dye is 3,3',5,5'-tetramethyl benzidine.

11. The composition of matter of claim 1, further comprising a surfactant.

12. The composition of matter of claim 11, wherein said surfactant is sodium dodecyl sulfonate.

13. The composition of matter of claim 1, wherein said extender is present in an amount ranging from about 1% to about 25% by weight of said composition.

14. The composition of matter of claim 13, wherein said extender is present in an amount ranging from abut 1% to about 10% by weight of said composition.

15. The composition of matter of claim 14, wherein said extender is present in an amount ranging from about 1% to about 3% by weight of said composition.

16. Analytical apparatus useful in determining an analyte in a sample comprising the composition of matter of claim 1 in the form of a film, and an inert carrier.

17. Method for determining an analyte in a sample comprising contacting said sample to the composition of matter of claim 1 and determining formation of a detectable signal formed by reaction of said analyte with said reagent system as an indication of said analyte.

18. Method for determining an analyte in a sample comprising contacting said sample to the analytical element of claim 16 and determining formation of a detectable signal formed by reaction of said analyte with said reagent system as an indication of said analyte.

19. The composition of matter of claim 1, wherein $R_1$, $R_3$ and $R_4$ are hydrogen and $R_2$ is phenyl.

20. A film-forming composition comprising:
    (i) an aqueous polymer emulsion wherein said polymer is formed of at least one monomer selected from the group consisting of

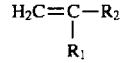

and

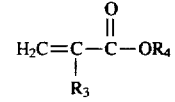

wherein $R_1$, $R_3$ and $R_4$, are the same or different, and are hydrogen or unsubstituted or substituted $C_1$–$C_6$ alkyl, and $R_2$ is a substituted or unsubstituted aromatic moiety;
    (ii) a reagent system for determination of an analyte; and
    (iii) an amount of an extender sufficient to reduce tackiness of said emulsion.

21. The film-forming composition of claim 20 coated on a substrate.

22. A film comprising a dried composition of claim 20.

* * * * *